(12) United States Patent
Bowlin et al.

(10) Patent No.: US 6,592,623 B1
(45) Date of Patent: Jul. 15, 2003

(54) ENGINEERED MUSCLE

(75) Inventors: Gary L. Bowlin, Mechanicsville; Gary Wnek, Midlothian; David G. Simpson, Mechanicsville, all of VA (US); Louis Terracio, Columbia, SC (US)

(73) Assignee: Virginia Commonwealth University Intellectual Property Foundation, Richmond, VA (US)

( * ) Notice: Subject to any disclaimer, the term of this patent is extended or adjusted under 35 U.S.C. 154(b) by 0 days.

(21) Appl. No.: 09/386,273

(22) Filed: Aug. 31, 1999

(51) Int. Cl.$^7$ .................................................. A61F 2/08
(52) U.S. Cl. .................................. 623/14.13; 623/13.17
(58) Field of Search ............................ 623/13.11–13.2, 623/14.13, 15.12

(56) References Cited

U.S. PATENT DOCUMENTS

| | | |
|---|---|---|
| 1,680,605 A | 8/1928 | Chen et al. |
| 3,892,648 A | 7/1975 | Phillips et al. |
| 4,043,331 A | 8/1977 | Martin et al. ............... 128/156 |
| 4,044,404 A | 8/1977 | Martin et al. ..................... 3/19 |
| 4,204,282 A * | 5/1980 | Bolt .................................... 3/1 |
| 4,634,443 A * | 1/1987 | Haber .......................... 623/14 |
| 4,657,793 A | 4/1987 | Fisher .......................... 428/36 |
| 4,705,518 A * | 11/1987 | Baker et al. .................. 623/14 |
| 4,738,740 A | 4/1988 | Pinchuk et al. |
| 5,256,418 A | 10/1993 | Kemp et al. ................. 424/423 |
| 5,378,469 A | 1/1995 | Kemp et al. ................. 424/423 |
| 5,460,962 A | 10/1995 | Kemp ......................... 435/238 |
| 5,580,859 A | 12/1996 | Felgner et al. ................. 514/44 |
| 5,655,517 A | 8/1997 | Coffee |
| 5,693,085 A | 12/1997 | Buirge et al. |
| 5,723,324 A | 3/1998 | Bowlin et al. |
| 5,787,567 A | 8/1998 | Miyazaki ..................... 29/596 |
| 5,813,614 A | 9/1998 | Coffee |
| 5,834,029 A | 11/1998 | Bellamkonda et al. |
| 5,902,741 A | 5/1999 | Purchio et al. |
| 5,906,934 A | 5/1999 | Grande et al. |
| 5,908,777 A | 6/1999 | Lee et al. .................... 435/320 |
| 5,910,488 A | 6/1999 | Nabel et al. .................. 514/44 |

(List continued on next page.)

FOREIGN PATENT DOCUMENTS

| | | |
|---|---|---|
| EP | 0 005 035 A1 | 10/1979 |
| EP | 0 266 035 A1 | 5/1988 |
| GB | 1 377 022 | 12/1974 |
| GB | 2142870 A | 1/1985 |
| RU | 2031661 | 3/1995 |
| WO | WO 91/01695 | 2/1991 |
| WO | WO 97/13849 | 4/1997 |
| WO | WO 98/03267 | 1/1998 |
| WO | WO 98/56894 | 12/1998 |

OTHER PUBLICATIONS

Modulation of Cardiac Myocyte Phenotype In Vitro by the Composition and Orientation of the Extracellular Matrix, Simpson et al., Journal of Cellular Physiology 161:89–105 (1994).

Electrospun Fiber Mats: Transport Properties, Gibson et al., Accepted AICHE, Oct. 98.

Electrospinning Polymer Fibers, Schreuder-Gibson, SSCN-C-YM, U.S. Army Natick Research, Development and Engineering Center, 1997.

(List continued on next page.)

*Primary Examiner*—Corrine McDermott
*Assistant Examiner*—Hieu Phan
(74) *Attorney, Agent, or Firm*—Kilpatrick Stockton LLP (57) ABSTRACT

A muscle implant includes an extracellular matrix, tendon and muscle cells. The extracellular matrix is made of a matrix of electrospun polymer fibers. The tendon is made of extruded collagen fibers and the muscle cells are disposed on the extracellular matrix in such a manner that the combination of components will functionally and structurally act as normal muscle tissue. Cardiac and smooth muscles may be similarly formed without tendons but including the extracellular matrix and muscle cells.

12 Claims, 8 Drawing Sheets

U.S. PATENT DOCUMENTS

| | | | |
|---|---|---|---|
| 5,915,377 A | 6/1999 | Coffee | |
| 5,948,654 A | 9/1999 | Tranquillo et al. | 435/174 |
| 6,057,137 A | 5/2000 | Tranquillo et al. | 435/174 |
| 6,068,199 A | 5/2000 | Coffee | |
| 6,096,347 A * | 8/2000 | Geddes et al. | 424/551 |
| 6,100,026 A | 8/2000 | Nova et al. | |
| 6,103,255 A | 8/2000 | Levene et al. | |
| 6,105,571 A | 8/2000 | Coffee | |
| 6,105,877 A | 8/2000 | Coffee | |
| 6,106,913 A | 8/2000 | Scardino et al. | 428/36.3 |
| 6,110,484 A | 8/2000 | Sierra | |
| 6,110,590 A | 8/2000 | Zarkoob et al. | 428/364 |
| 6,117,296 A * | 9/2000 | Thomson | 204/607 |
| 6,121,042 A | 9/2000 | Peterson et al. | |
| 6,146,892 A | 11/2000 | Ma et al. | |
| 6,179,872 B1 | 1/2001 | Bell et al. | |
| 6,197,575 B1 | 3/2001 | Griffith et al. | |
| 6,245,345 B1 | 6/2001 | Swanbom et al. | |
| 6,252,129 B1 | 6/2001 | Coffee | |
| 6,254,627 B1 | 7/2001 | Freidberg | |
| 6,265,333 B1 | 7/2001 | Dzenis et al. | |
| 6,306,424 B1 | 10/2001 | Vyakarnam et al. | |
| 6,318,640 B1 | 11/2001 | Coffee | |

OTHER PUBLICATIONS

Neonatal Rat Heart Cells Cultured In Simulated Microgravity, Akins et al., In Virto Cell. Dev. Biol.—Animal 33:337–334, May 1997.

Microgravity Tissue Engineering, Freed et al., In Vitro Cell. Dev. Biol.—Animal 33:381–385, May 1997.

Establishment Of A Three–Dimensional Human Prostate Organoid Coculture Under Microgravity–Simulated Conditions: Evaluation Of Androgen–Induced Growth And PSA Expression, Zhau et al., In Vitro Cell. Dev. Biol.—Animal 33:375–380, May 1997.

Three–Dimensional Culture Of Bovine Chondrocytes In Rotating–Wall Vessels, Baker et al., In Vitro Cell. Dev. Biol.—Animal 33:358–365, May 1997.

Skeletal Muscle Satellite Cells Cultured In Simulated Microgravity, Molnar et al., In Vitro Cell. Dev. Biol.—Animal 33:386–391, May 1997.

Myoblast Seeding In A Collagen Matrix Evaluated in vitro, van Wachem et al., Journal of Biomedical Materials Research, vol. 30, 353–360 (1996).

Letter to the Editor, A Simplified Method For Tissue Engineering Skeletal Muscle Organoids in vitro, Shansky et al, In Vitro Cell. Dev. Biol.–Animal 33:659–661, Oct. 1997.

Tissue Engineering Skeletal Muscle: Preparation Of Highly Dense, Highly Oriented Hybrid Muscular Tissues, Okano et al., Cell Transplantation, vol. 7, No. 1, pp. 71–82, 1998.

Hybrid Muscular Tissues: Preparation Of Skeletal Muscle Cell–Incorporated Collagen Gels, Okano et al., Cell Transplantation, vol. 6, No. 2, pp. 109–118, 1997.

Cardiomyocyte Transplantation In A Porcine Myocardial Infarction Model, Watanabe et al., Cell Transplantation, vol. 7, No. 3, pp. 239–246, 1998.

Atomic Force Microscopy Of Structures Produced By Electrospraying Polymer Solutions, Morozov et al., International Journal of Mass Spectrometry 178, pp. 143–159, 1998.

Nanometre Diameter Fibres Of Polymer, Produced By Electrospinning, Reneker et al., Nanotechnology 7, pp. 216–223, 1996.

Collagen Fabrics As Biomaterials, Cavallaro et al, Biotechnology and Bioengineering, vol. 43, pp. 781–791. 1994.

Mechanical Properties of Collagen Fibres: A Comparison Of Reconstituted And Rat Tail Tendon Fibres, Kato et al., Biomaterials, vol. 10, Jan. 1989.

Formation Of Continuous Collagen Fibres: Evaluation Of Biocompatibility And Mechanical Properties, Kato et al., Biomaterials, vol. 11, Apr. 1990.

Regenertion In Grafts Of Normal And Denervated Rat Muscles, Carlson et al., Phlugers Arch, 353, pp. 215–225, 1975.

Isolation And Characterization of Human Muscle Cells, Blau et al., Proc. Natl. Acad. Sci. USA, vol. 78, No. 9, pp. 5623–5627, Sep. 1981.

Cell Shape and Growth Regulation In Skeletal Muscle: Exogenous Versus Endogenous Factors, Vandenburgh, Journal Of Cellular Physiology 116:363–371, 1983.

Mechanical Stimulation Of Organogenic Cardiomyocyte Growth in vitro, Vandenburgh et al., The American Physiological Society, pp. c1284–1292, 1996.

Mechanically Induced Orientation Of Adult Rat Cardiac Myocytes In Vitro, Samuel et al., In Vitro Cell. Dev. Biol. 26:905–914, Sep. 1990.

In Vitro Model for Stretch–Induced Hypertrophy of Skeletal Muscle, Vandenburgh, Science, vol. 203, pp. 265–268, Jan. 19, 1979.

Engineering Smooth Muscle Tissue With A Predefined Structure, Kim et al., Department of Chemical Engineering, University Of Michigan, 1997.

Mechanically Induced Alterations In Cultured Skeletal Muscle Growth, Vandenburgh et al., J. Biomechanics, vol. 24, Suppl. I, pp. 91–99, 1991.

Skeletal Muscle Growth Is Stimulated By Intermittent Stretch–Relaxation In Tissue Culture, Vandenburgh et al., American Physiological Society, pp. C674–C682, 1989.

Dynamic Mechanical Orientation Of Skeletal Myofibers In Vitro, Vandenburgh, Developmental Biology 93, pp 438–443, 1982.

Letter to Editor, A Simplified Method For Tissue Engineering Skeletal Muscle Organoids In Vitro, In Vitro Cell. Dev. Biol.—Animal 33:659–661, 1991.

Mechanical Forces And Their Second Messengers In Stimulating Cell Growth in vitro, Vandenburgh, American Physiological Society, pp. R350–355, 1992.

Attenuation Of Skeletal Muscle Wasting With Recombinant Human Growth Hormone Secreted From A Tissue–Engineered Bioartificial Muscle, Vandenburgh et al., Human Gene Therapy 9:2555–2564, Nov. 1998.

Optimizing Seeding And Culture Methods To Engineer Smooth Muscle Tissue On Biodegradable Polymer Matrices, Kim et al., Biotechnology And Bioengineering, vol. 57, No. 1, pp. 46–54, 1998.

Highly Oriented, Tubular Hybrid Vascular Tissue For A Low Pressure Circulatory System, Hirai, et al., ASAIO Journal, pp. M383–388, 1994.

Transplantation Of Genetically Marked Cardiac Muscle Cells, Gojo et al., The Journal Of Thoracic and Cardiovascular Surgery, vol. 113, No. 1, pp. 10–18, 1997.

Formation of Nascent Intercalated Disks Between Grafted Fetal Cardiomyocytes and Host Myocardium, Soonpaa et al., Science, vol. 264, pp. 98–101, 1994.

Skeletal Myoblast Transplantation For Repair of Myocardial Necrosis, Murry et al., The American Society for Clinical Investigation, Inc., vol. 98, No. 11, pp. 2512–2523, Dec. 1996.

Long-Term Survival of AT-1 Cardiomyocyte Grafts In Syngeneic Myocardium, Koh et al., The American Physiological Society, pp. H1727–1733, 1993.

Natural History of Fetal Rat Cardiomyocytes Transplanted Into Adult Rat Myocardial Scar Tissue, Li et al., American Heart Association, Inc., Supplement II Circulation, vol. 96, No. 9, pp. II–179 to II–187Nov. 1997.

In Vivo Survival and Function of Transplanted Rat Cardiomyocytes, Li et al., American Heart Association, Inc., Circulation Research, vol. 78, No. 2, pp. 283–288, Feb. 1996.

Effects of Static Axial Strain on the Tensile Properties and Failure Mechanisms of Self–Assembled Collagen Fibers, Pins et al., University of Medicine and Denistry of New Jersey, Robert Wood Johnson Medical School, pp. 1429–1440, Dec. 22, 1997.

Self–Assembly of Collagen Fibers, Influence of Fibrillar Alignment and Decorin on Mechanical Properties, Pins et al., Biophysical Journal, vol. 73, pp. 2164–2172, Oct. 1997.

Type I Collagen in Solution, Silver et al., The Journal of Biological Chemistry, vol. 255, No. 19, pp. 9427–9433, 1980.

Experimental Investigation of Scaling Laws for Electrospraying: Dielectric Constant Effect, Chen et al., Aerosol Science and Technology, 27:3, pp. 367–380, Sep. 1997.

Electrospraying of Conducting Liquids for Monodisperse Aerosol Generation In the 4 nm to 1.8$\mu$m Diameter Range, Chen et al., Particle Technology Laboratory, Mechanical Engineering Department, University of Minnesota, pp. 963–977,1995.

Electrospinning Process and Applications of Electrospun Fibers, Doshi et al., Journal of Electrostatics, 35, pp. 151–160, 1995.

Regeneration of the Completely Excised Gastroanemius Muscle in the Frog and Rat From Minces Muscle Fragments, Carlson, J. Embryol. Exp. Morph., vol. 125, pp 447–472.

Tissue Engineering of Skeletal Muscle, Highly Dense, Highly Oriented Hybrid Muscular Tissues Biomimicking Native Tissues, ASAIO Journal 1997; 43:M749–M753.

Survival of Embryonic Cardiac Myocytes Transplanted Into Host Rat Soleus Muscle, Connold et al., Journal of Muscle Research and Cell Motility 16, 481–489, 1995.

Tissue Engineered Skeletal Muscle: Preparation Of Highly Dense, Highly Oriented Hybrid Muscular Tissue, Okano, Cell Transplantation, vol. 7, No. 1, pp. 71–82, 1998.

Regulation of New Blood Vessel Growth Into Ischemic Skeletal Muscle, Bush et al., Journal of Vascular Surgery, vol. 28, No. 5, pp. 919–928, 1998.

Controlled Delivery Of Vascular Endothelial Growth Factor Promotes Neovascularization And Maintains Limb Function In A Rabbit Model Of Ischemia, Hopkins et al., Journal of Vascular Surgery, vol. 27, No. 5, pp. 886–895, 1997.

Revascularization Of Skeletal Muscle Transplanted Into The Hamster Cheek Pouch: Electron Microscopy, Weiss et al., Microvascular Research, vol. 26, pp. 65–73, 1983.

Mechanism Of Compensatory Hypertrophy In Skeletal Muscle Of The Rat, Gutmann et al., Experimental Neurology, vol. 31, pp. 451–464, 1971.

Identification Of Self–Renewing Myoblasts In the Progeny Of Single Human Muscle Satellite Cells, Baroffio et al., Differentiation, vol. 60, pp 47–57, 1996.

Patterned Growth Of Neonatal Rat Heart Cells In Culture, Rohr et al., Circulation Research, vol. 68, No. 1, pp. 114–130, 1991.

Cardiomyocyte Transplantation In A Porcine Myocardial Infarction Model, Watanabe et al., Cell Transplantation, vol. 7, No. 3, pp. 239–246, 1998.

Hybrid Muscular Tissues: Preparation of Skeletal Muscle Cell–Incorporated Collagen Gels, Okano et al., Cell Transplantation, vol. 6, No. 2, pp. 109–118, 1997.

Myoblast Seeding In A Collagen Matrix Evaluated in vitro, Wachem et al., Journal of Biomedical Materials Research, vol. 30, pp. 353–360, 1996.

The Biomedical Engineering Handbook, Joseph D. Bronzino, 1995, pp. 637–644.

EKOMEDSERVIS: WPI World Patent Information Derwent, Derwent, GB', WPI World Patent Information Derwent, Derwnet, GB, vol. 44, Nr. 95, London, GB, (XP002046663), Mar. 27, 1995 (Abstract only).

Esquivel, C., et al., "Why Small Caliber Vascular Grafts Fail: A Review of Clinical and Experimental Experience and the Significance of the Interaction of Blood at the Interface," Journal of Surgical Research, 1986, pp. 1–15, vol. 41.

Freed, L. E., et al., "Biodegradable Polymer Scaffolds for Tissue Engineering," Bio/Technology, Jul. 1994, pp. 689–693, vol. 12.

Kanda, K., eta al., "In Vitro Reconstruction of Hybrid Vascular Tissue Hierarchic and Oriented Cell Layers," ASAIO Journal, 1993, pp. M561–M565, vol. 39.

Kanda, K., et al., "Mechanical Stress–Induced Orientation and Ultrastructural ChanGe of Smooth Muscle Cells Cultured in Three–Dimensional Collagen Lattices," Cell Transplantation, 1994, pp. 481–492, vol. 3.

L'Heureux, N., et al., "A Completely Biological Tissue–Engineered Human Blood Vessel," The FASEB Journal, Jan. 1998, pp. 47–56, vol. 12.

Mikos, A. G., et al., "Wetting of poly(L–lactic acid) and poly(DL–lactic–co–glycolic acid) foams for tissue culture," Biomaterials, 1994, pp. 55–58, vol. 15, No. 1.

Mooney, D. J. et al., "Design and Fabrication of Biodegradable Polymer Devices to Engineer Tubular Tissues," Cell Transplantation, 1994, pp.203–210, vol. 3, No. 2.

Weinberg, C. B., et al., "A Blood Vessel Model Constructed from Collagen and Cultured Vascular Cells," Science, Jan. 24 1986, p. 397, vol. 231.

Zund, G., et al., "Tissue Engineering: A new approach in cardiovascular surgery; Seeding of human fibroblasts followed by human endothelial cells on resorbable mesh," European Journal of Cardio–thoracic Surgery, 1998, pp. 160–164, vol. 13.

Ferber, D., "Lab–Grown Organs Begin to Take Shape", Science, 1999, pp. 422–424, vol. 284.

Gershon, B. et al., "Utilization of composite laminate theory in the design of synthetic soft tissues for biomedical prostheses", Biomaterials, Casali Institute of Applied Chemistry, Graduate School of Applied Science and Technology, The Hebrew University of Jerusalem, Oct. 1990, pp. 548–552, vol. 11, No. 8.

Niklason, L. E. et al., "Functional Arteries Grown in Vitro", Science 1999, pp. 489–493, vol. 284.

Rodeo, S. A., "New and Emerging Treatments for Cartilage and Meniscus Injuries," MD Vista J. Medicine, 2000, pp.1–4.

Sabelman, E. E., et al., "Composite Cell/Tissue Replacement for Nerve and Pressure Sore Repair," http://guide.Stanford.edu/Publications/clinB.html, Republished from the 1994 Veteran's Administration Rehabilitation Research and Development Center Progress Report, pp. 1–2.

Tiollier, J. et al., "Fibroblast Behavior on Gels of Type I, III, and IV Human Placental Collagens", Exp. Cell Res., 1990, pp. 95–104, vol. 191.

Wong, W. H. et al., "Synthesis and Properties of Biodegradable Polymers Used as Synthetic Matrices for Tissue Engineering", Synthetic Biodegradable Polymer Scaffolds, 1997, pp. 51–82, Chp. 4.

Electrospinning Process and Applications of Electrospun Fibers, Doshi et al., Journal of Electrostatics, 35 (1995) 151–160.

European Search Report, PCT/US 00/20974.

* cited by examiner

ENGINEERED MUSCLE

This invention relates to a muscle implant designed for transplantation. The implant is both a functional and structural replacement for dysfunctional muscle tissue.

BACKGROUND OF THE INVENTION

Muscle abnormalities are a fact of life whether they result from a developmental anomaly or from a traumatic injury or for any other reason. Structural defects to striated muscle tissue range from relatively functionally benign to profoundly debilitating disorders. In any circumstance, the condition can affect the patient on a number of different levels. For example, structural defects to the musculature of the face may have a minor impact on the ability of a patient to survive. However, even minor cosmetic defects of the muscle of the face can have substantial psychological implications.

In addition to the striated muscle abnormalities noted above, cardiovascular muscles are also subject to deterioration and disease. Congenital malformations of the heart are also common. Conventional surgical techniques are fundamentally unable to adequately restore the subtle structural and functional relationships that exist in a healthy heart. An intact heart has an elaborate three-dimensional structure that insures the orderly propagation of electrical signals and the coordinated contraction of the ventricular wall. If the heart muscle is to be effectively repaired, the three-dimensional organization must be addressed at the cellular level.

Very few alternative technologies exist for the reconstruction of dysfunctional skeletal muscle tissue. Attempts to fabricate such tissue have been generally confined to experiments in which skeletal muscle cells are trapped in a collagen gel. In these experiments, the cells have been seeded onto the exterior of a collagen gel or literally enveloped within the gel as it is polymerized. Subsequently, the cells are allowed to differentiate within the random, "three-dimensional" environment of the collagen gel. The distribution of cells within these collagen gels represents a limiting factor in these constructions. When muscle cells are seeded onto the exterior of a collagen gel they typically remain concentrated on the peripheral regions of the gel. Experiments in which muscle cells are directly incorporated into a collagen gel as it undergoes polymerization have yielded more densely and uniformly populated cultures; however, these constructions remain less dense than their in vivo counterparts. More importantly, the implants produced in conventional tissue culture are composed of muscle cells that lack a uniform alignment or orientation. The random nature of the cells within these sparsely populated implants limits the utility of that tissue and its ability to function as an ordinary muscle.

Additional constraints that must be addressed in designing an implant include the mechanical stability of the implant. The implant must have enough structural integrity to withstand manual manipulation, the surgical procedures and the mechanical environment of the intact tissue. Intact skeletal muscle is surrounded in vivo by multiple layers of a dense connective tissue that compartmentalizes the muscle and reinforces the structure of the tissue. Mimicking the specific structure of this arrangement in vitro is difficult, because any dense, investing material will tend to limit nutrient diffusion, oxygen transport and the removal of metabolic waste products away from the cells. Components made from artificial materials such as polyester mesh have been used with some success to increase the strength of the cultures while allowing them to retain a substantial portion of their elastic properties. However, the incorporation of synthetic materials into an implant can increase the likelihood that it will initiate an inflammatory response in vivo.

Cardiac tissue lacks a dense connective tissue. However, the muscle cell of the heart is organized into a complicated lattice. The individual muscle cells of the heart have a rod-like cell shape. Like skeletal muscle, they are oriented along a common axis in a complex three-dimensional pattern. Each cell of the heart is invested with a basement membrane and interconnected to its neighbors by a complex matrix of collagen fibrils. The three dimensional pattern of the cell layers within the heart is critical for the orderly propagation of electrical signals and the coordinate contraction of the ventricular wall.

Smooth muscle surrounds the supports of many of the hollow organs. For example, in the gut it surrounds the stomach and intestinal track. Contraction of this muscle mixes food and propels it along the digestive track. In the cardiovascular system smooth muscle cells surround the walls of the arteries and large veins and functions to control the caliber of the vessels. Smooth muscle lacks the nearly uniform cell shape and lattice like distribution of skeletal and cardiac muscle cells. However, smooth muscle cells do exhibit an elongated, bipolar cell shape. As a population they are organized along a similar axis in a series of overlapping cellular layers. This pattern of organization allows smooth muscle to exert contractile forces in a complex pattern.

SUMMARY OF THE INVENTION

Accordingly, it is an object of the present invention to overcome the foregoing drawbacks and to provide a muscle implant to a host in need thereof. The implant can be used in a variety of ways including to augment existing muscle, correct muscle deficiencies or as a functional and structural replacement for dysfunctional muscle tissue. Further, the invention includes a method for manufacturing the muscle implant.

In one embodiment, a muscle implant includes an extracellular matrix made of electrospun fibers and muscle cells disposed on the matrix. In another embodiment, the muscle implant comprises an extracellular matrix made of electrospun fibers for supporting muscle, a tendon made of extruded fibers, and a muscle cell layer that is disposed on the extracellular matrix. The muscle cell layer can be multilayered. In other variations, the electrospun fibers may be cross linked. Also, an oriented layer of collagen can be deposited onto the extracellular matrix so that the muscle cells are disposed onto the oriented layer of collagen.

In another embodiment, the invention includes an extracellular matrix for supporting muscle comprising a matrix of electrospun fibers. The fiber is discharged from an electrically charged orifice onto a grounded substrate to form the matrix. The matrix can also be treated with cross linking agents so that the fibers are cross linked.

The invention also includes a method of manufacturing an extracellular matrix comprising extruding electrically charged polymer solution onto a grounded target substrate under conditions effective to deposit polymer fibers on the substrate to form an extracellular matrix. The extruded polymer may form a three-dimensional matrix. The extracellular matrix may further include a gel of aligned collagen fibers deposited thereon.

In a further embodiment, the invention includes a method of forming a muscle fascial sheath by providing an electrically grounded substrate. There is further provided a reservoir of collagen solution wherein the reservoir has an orifice that allows the collagen solution to leave the reservoir. The collagen solution is electrically charged and then streamed onto the substrate to form a muscle fascial sheath.

In still a further embodiment, the invention includes a method of layering muscle cells on an extracellular matrix. The method includes providing an extracellular matrix and then placing the extracellular matrix inside a rotating wall bioreactor. A culture medium is loaded into the bioreactor wherein the medium comprises muscle cells. The bioreactor is then run until muscle cells attach to the extracellular matrix. Alternatively, the muscle cells attached to the extracellular matrix form multiple layers.

DETAILED DESCRIPTION OF A PREFERRED EMBODIMENT

An engineered muscle implant can comprise one or more of the following components. They are an engineered extracellular matrix, an engineered tendon, and engineered muscle cells. Each component will be discussed in detail separately and then in combination with respect to their assembly.

A. Engineered Extracellular Matrix for Supporting Muscle

In a normal human anatomy, muscles are bundles of oriented muscle cells that are encased in an outer protective coating which we refer to as an extracellular matrix. In skeletal muscle, this outer coating is referred to as the fascial sheath. The fascial sheath gives shape and support to the skeletal muscle. The fascial sheath is the extracellular matrix or scaffolding that maintains the integrity of the muscle. Smooth muscle and cardiac muscle is also supported by an extracellular matrix. The cells of smooth and cardiac tissue are both interconnected by a network of collagen fibrils. Smooth muscle lacks a defined fascial sheath. The entire surface of the heart is enclosed in a tough outer coating of connective tissue composed of collagen called the pericardium.

The engineered extracellular matrix of the present invention can be custom constructed to meet the requirements of skeletal, smooth or cardiac muscles. In preferred embodiments, the extracellular matrix is fabricated by electrospinning polymer fibers (synthetic or natural) to form a matrix directly onto a substrate; or to form a matrix directed onto a substrate or form (mold), or other surface such as the central cylinder of the RCCS Bioreactor (Synthecon).

There are a number of different kinds of bioreactors, devices designed to provide a low-shear, high nutrient perfusion environment, available on the market. Until recently, most of the available bioreactors maintained cells in suspension and delivered nutrients and oxygen by sparging, through the use of impellers, or other means of stirring. The RCCS bioreactor is a rotating wall bioreactor. It consists of a small inner cylinder, the substrate for the electrospinning process, positioned inside a larger outer cylinder. Although the electrospun matrix can be fabricated on the inner cylinder, other locations within the bioreactor also may be used for placement of the matrix for seeding. The gap between the inner and outer cylinders serves as the culture vessel space for cells. Culture medium is oxygenated via an external hydrophobic membrane. The low shear environment of the Synthecon RCCS bioreactor promotes cell-cell and cell-extracellular matrix (ECM) interactions without the damage or "washing away" of nutrients that occurs with active stirring or sparging. Typically, the RCCS device is operated at rotation rates of 8 up to 60 RPM, as required to maintain cells in suspension, and at less than 8 RPM (preferably 2–3 RPM) for cultures immobilized along the center shaft of the vessel. The Synthecon bioreactor can be used in a standard tissue culture incubator.

Figure 1:
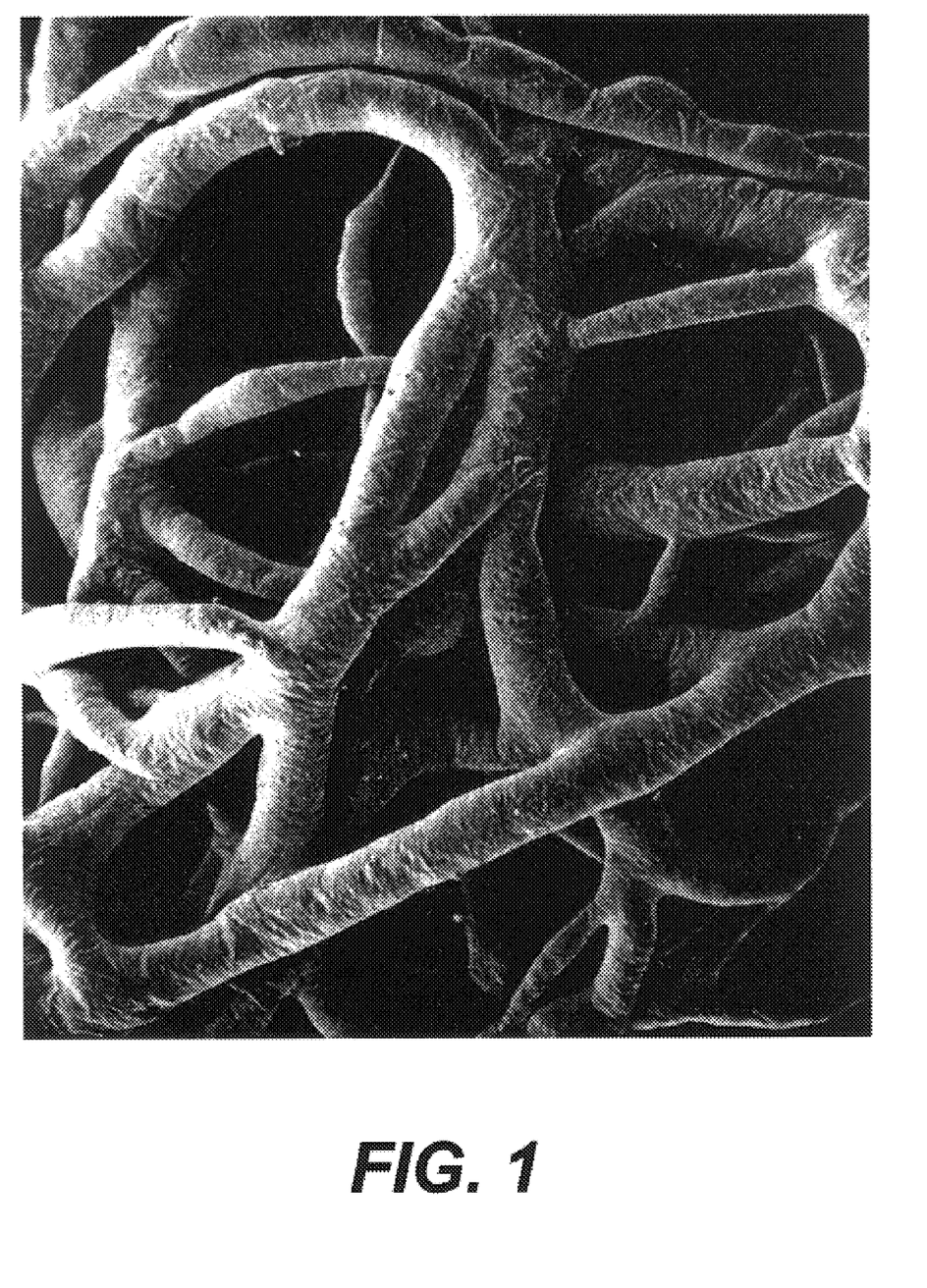
FIG. 1 is a scanning electron micrograph of an electrospun matrix of fibers.

The electrospinning process can be used to produce a dense, mat-like matrix of unoriented polymer fibers (FIG. 1). "Electrospinning" means a process in which fibers are formed from a solution or melt by streaming an electrically charged polymer solution or melt through an orifice. Electrospinning has been used in the textile industry to produce ultra thin layers of fiber fabrics (continuous multi filaments) and dense mats of material. The polymer fibers formed by this technique are in the 40–500 nanometer diameter range. The mechanical properties (i.e., strength), porosity, and weight of the fabrics produced by electrospinning can be controlled by regulating the processing conditions, the materials used in the fabrication process and the thickness of the deposited material. Gibson, P. W., et al., Electrospun Fiber Mats: Transport Properties, 1998 AIchE J.; Deshi, J., et al., Electrospinning Process and Applications of Electrospun Fibers, 1996 J. Electrostatics 35:151.

Figure 2A:
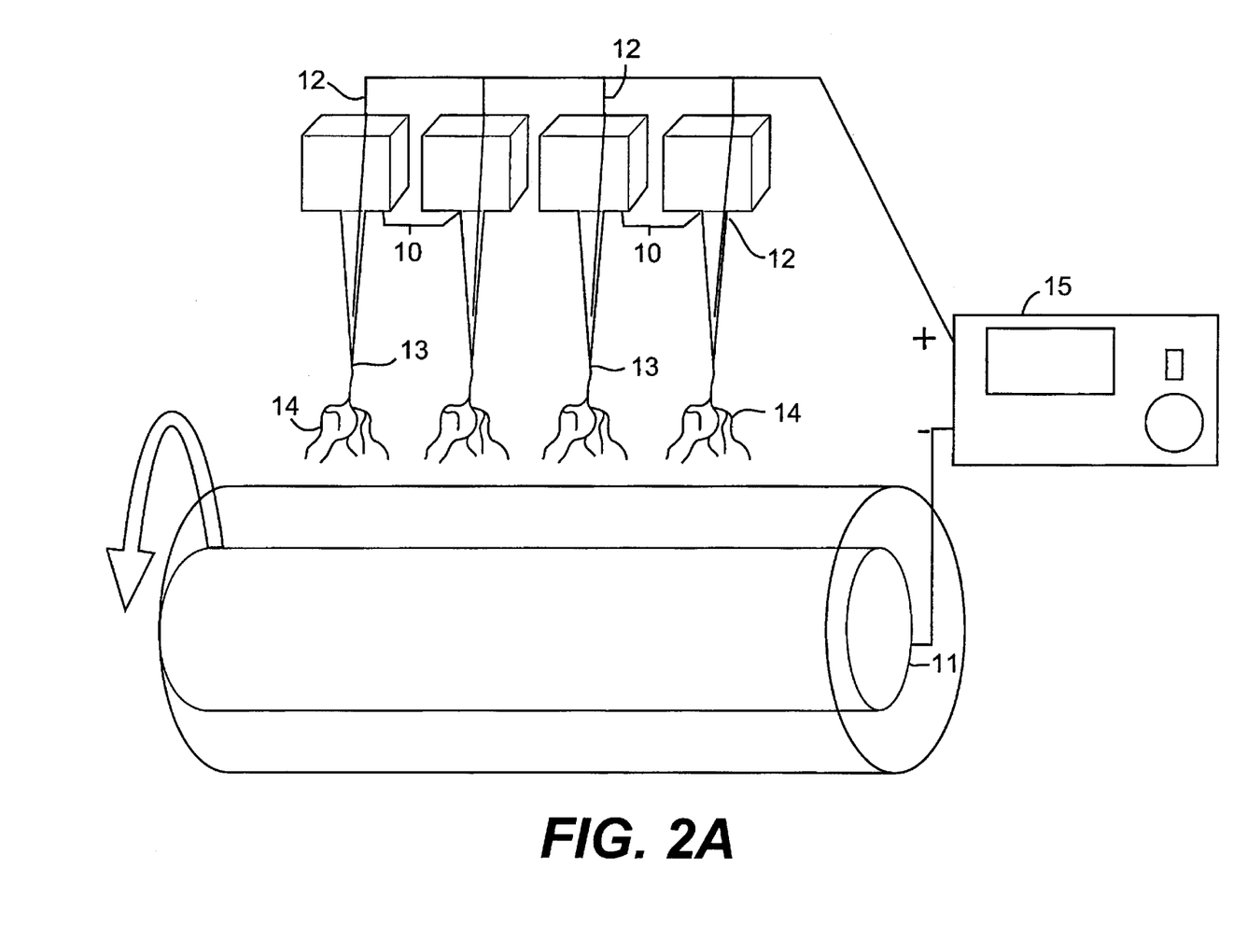
FIGS. 2A and 2B are schematic drawings of electrospinning devices including the electrospinning equipment and a rotating wall bioreactor.
Figure 2B:
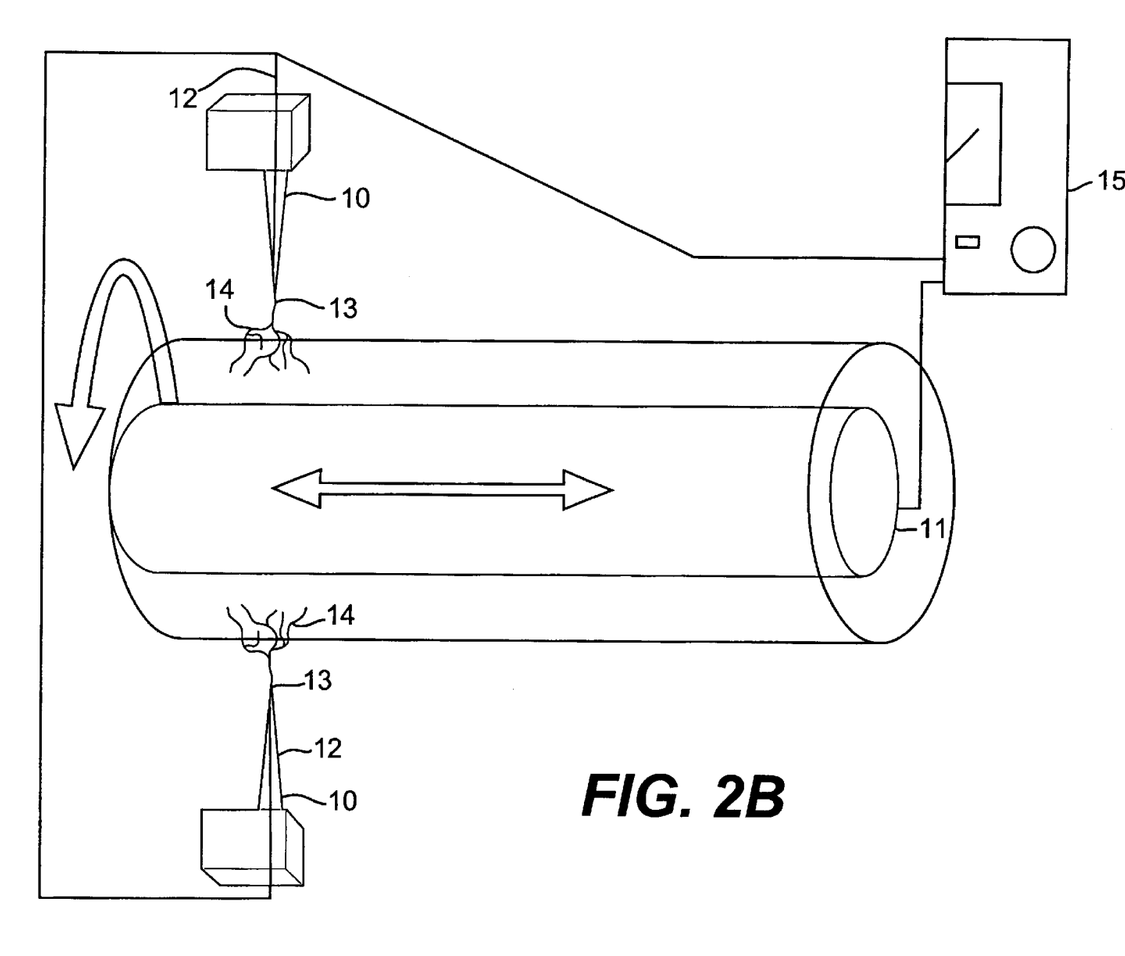

An extracellular matrix of electrospun fibers in accordance with the present invention can be produced analogously. While any polymer can be used, it is preferable to electrospin natural polymer fibers such as collagen fibers. Various effective conditions can be used to electrospin a collagen matrix. While the following is a description of a preferred method, other protocols can be followed to achieve the same result. Referring to FIGS. 2A and 2B, in electrospinning collagen fibers, micropipettes 10 are filled with a solution of collagen and suspended above a grounded target 11, for instance, a metal ground screen placed inside the central cylinder of the RCCS bioreactor. A fine wire 12 is placed in the solution to charge the collagen solution in each pipette tip 13 to a high voltage. At a specific voltage determined for each solution and apparatus arrangement, the collagen solution suspended in the pipette tip is directed towards the grounded target. This stream 14 of collagen forms a continuous filament that, upon reaching the grounded target, collects and dries to form a three-dimensional, ultra thin, interconnected matrix of collagen (fabric). Minimal electrical current is involved in this process, and, therefore, the streaming process does not denature the collagen, because there is no expected temperature increase in the collagen solution during the procedure.

Various polymers can be used alone, or in combination, to produce the electrospun matrix. In preferred embodiments, collagen is used to form the extracellular matrix. Any suitable collagen can be used, including, types I through X. In preferred embodiments, types I and III are used. Collagens are available from commercial sources, or they can be prepared according to methods known in the art.

A variety of material can be supplemented into the electrospinning solution. DNA coding for desired products (vectors) can be mixed into the electrospinning polymeric solution for incorporation into the tissue-engineered scaffold. Upon consumption/reorganization of the scaffolding by the seeded cells, they may incorporate the vector (i.e. genetic engineering) into their DNA and produce a desired affect. The DNA can be in any form which is effective to enhance its uptake into cells. For example, it can be naked (e.g., U.S. Pat. Nos. 5,580,859; 5,910,488) or complexed or encapsulated (e.g., U.S. Pat. Nos. 5,908,777; 5,787,567). Similar to adding DNA, it may be possible to incorporate growth factors or other chemotaxins such as angiogenic factors into the electrospun matrix to aid in tissue regeneration.

The electrospinning process can be manipulated to meet the specific requirements for any given application. The micropipettes can be mounted on a frame that moves in the x, y and z planes with respect to the grounded substrate. In this way, the collagen or other polymer streamed from the micropipette can be specifically aimed or patterned. Although the micropipettes can be moved about manually, preferably, the frame onto which the micropipettes are mounted is controlled by a microprocessor and a motor that allows the pattern of streaming collagen to be predetermined by a person making a specific matrix. For instance, collagen fibers can be oriented in a specific direction, they can be layered, or they can be programmed to be completely random and unoriented.

In the electrospinning process, the polymer stream can branch out to form fibrils of the polymer. The degree of branching can be varied by many factors including, but not limited to, voltage, ground geometry, distance from micropipette tip to the substrate, diameter of micropipette tip, polymer concentration, etc. These variables are well-known to those of skill in the art of electrospinning microfiber textile fabrics.

The geometry of the grounded target can be modified to produce a desired matrix. In a preferred embodiment, a rotating wall bioreactor is used. The grounded target is a cylinder that fits inside the inner cylinder in the electrospinning process. By varying the ground geometry, for instance having a planar or linear or multiple points ground, the direction of the streaming collagen can be varied and customized to a particular application. For instance, a grounded target comprising a series of parallel lines can be used to orient electrospun collagen in a specific direction. The grounded target may be a cylindrical mandrel whereby a tubular matrix is formed. Most preferably, the ground is a variable surface that can be controlled by a microprocessor that dictates a specific ground geometry that is programmed into it. Alternatively, for instance, the ground may be mounted on a frame that moves in the x, y, and z planes with respect to a stationary micropipette tip streaming collagen. The grounded target 11 in FIG. 2B is shown as being able to oscillate along its longitudinal axis.

The substrate onto which the collagen is streamed can be the grounded target itself or it can be placed between the micropipette tip and the grounded target. The substrate can be specifically shaped, for instance in the shape of a heart or a part thereof or a vascular graft, to substitute or replace a specifically shaped muscle.

Figure 7:
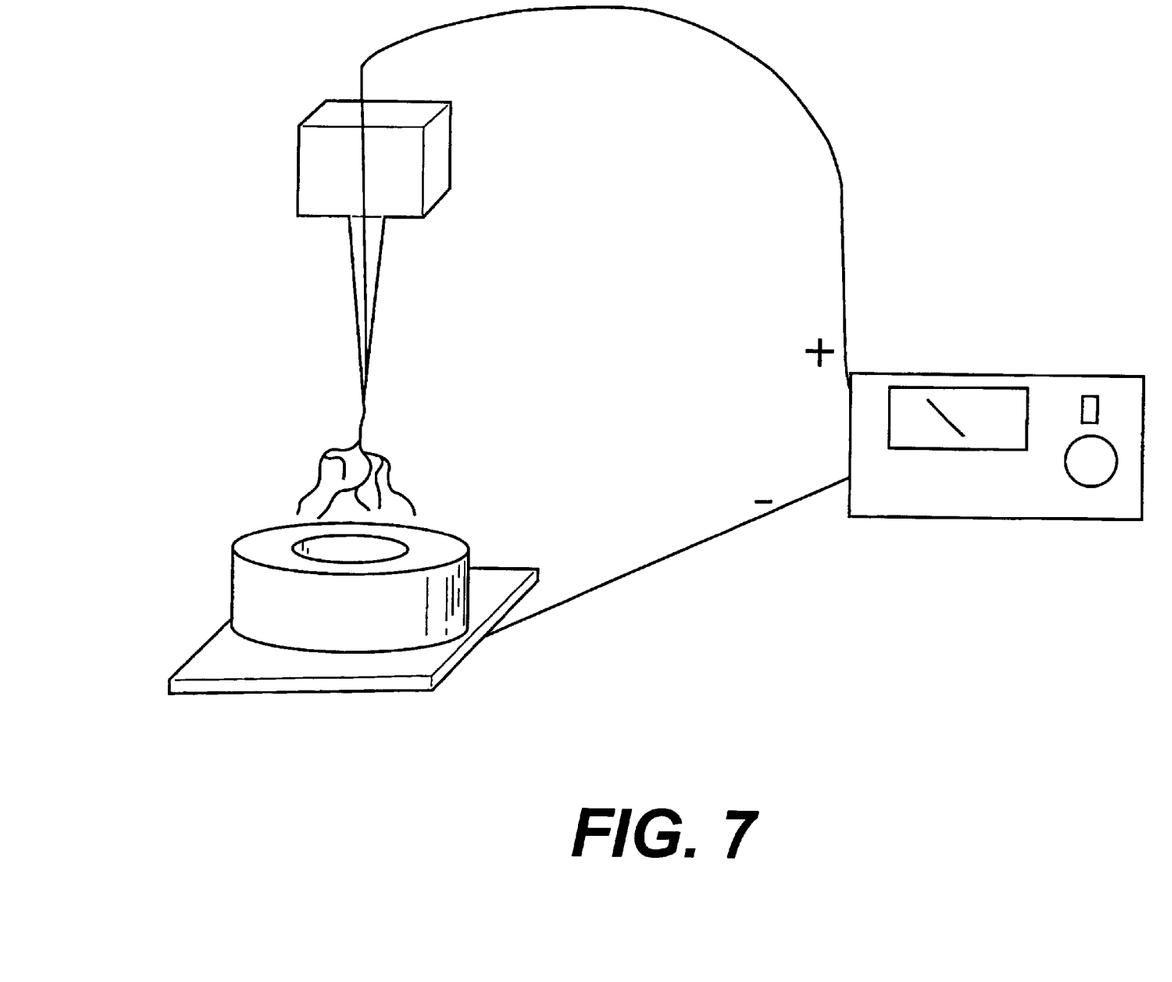
FIG. 7 is a schematic representation of a form into which the polymer stream may be directed.

Through modification of a substrate shape and by programming the specific orientation and density of the electrospun polymer, a very complex muscle pattern can be replicated to enable a specific muscle form for a specific application to be created. Alternatively, for example, collagen may be streamed into a preselected form. The thickness and attributes of the matrix may be preselected to form cartilage, dentin packing, or other similar prosthesis. A schematic example of this type of application is shown in FIG. 7.

Other variations on electrospinning include:
1. Using different solutions (e.g.,. collagen I and III) to produce two or more different fibers simultaneously (matrix fiber array). In this case, the single component solutions can be maintained in separate reservoirs.
2. Using mixed solutions (e.g., collagen I and III) in the same reservoir(s) to produce fibers composed of multiple polymers (fiber composition "blends"). Nonbiological but biologically compatible material can be mixed with a biological molecule such as collagen, e.g., PVA, PLA, PGA, PEO, etc.
3. Utilizing multiple potentials applied for the different solutions or even the same solutions.
4. Having two or more different geometric grounded targets (i.e. small and large mesh screens).

All these variations can be done separately or in combination with each other to produce a wide variety of electrospun extracellular matrices.

The stability, rigidity, and other attributes of the electrospun matrix can be regulated by the degree to which it is chemically modified. The electrospun matrix may be used in its unmodified state, or it may be modified in accordance with the requirements of a specific application. Modifications to the matrix can be made during the electrospinning process or after it is deposited. Cross-linking agents such as carbodiimide EDC (1-ethyl-3(3 dimethyl aminopropyl)), carbodiimide hydrochloride, NHS (n-hydroxysuccinimide), or UV light can be used e.g., to stabilize the fascial sheath against proteolytic attack, and/or to increase the stability of collagen gels. See, e.g., Van Wachem, et al., 1996 Myoblast seeding in a collagen matrix evaluated in vitro, J. Biomedical Materials Res. 30:353–60.

B. Engineered Tendon

The engineered tendon, or the connective tissue struts that anchor the engineered muscle to bone, can be assembled from extruded collagen fibers or other suitable materials. Collagen fibers are preferred, because collagen is less likely to be rejected by a recipient's immune system. These fibers function in combination with the extracelluar matrix to stabilize the overall structural integrity of the muscle implants. Collagen fibers for the fabrication of the engineered tendon can be extruded after known methods. Kato, Y. P. and Silver, F. H., Formation of Continuous Collagen Fibers: Evaluation of Biocompatibility and Mechanical Properties, 1990 Biomaterials 11: 169–75; Kato, Y. P., et al., Mechanical Properties of Collagen Fibers: A Comparison of Reconstituted Rat Tendon Fibers, 1989 Biomaterials 10:38–42; and U.S. Pat. Nos. 5,378,469 and 5,256,418 to Kemp, et al.

A preferred collagen extrusion apparatus comprises a syringe pump, microbore tubing, a dehydration trough, recirculation pump, rinsing trough, drying chamber, heating air dryer, and a collagen fiber winder. The syringe is filled with degassed collagen and mounted onto a syringe pump. The collagen solution is then extruded from the syringe, through the microbore tubing, and into a dehydration bath (Polyethylene glycol in PBS). The formed collagen fiber is subsequently guided through a rinsing bath (phosphate buffered saline, PBS) and attached to a winding system within a dryer. Once the initial fiber has been formed and attached to the winding element, the process becomes automated and continuous. At an extrusion rate of approximately 8 cm/minute, the extrusion apparatus can produce fiber 1–10 meters in length and 50–250 $\mu$m in diameter. After production, the fiber diameter can be verified through scanning electron and light microscopic evaluation. Varying the reaction conditions controls the diameter of the collagen fiber that is polymerized. The physical properties of the engineered collagen fiber can be further modified and controlled by regulating the composition of the extrusion material. The elastic properties of the engineered tendon can be modulated by incorporated elastin, fibrin or man made material into the collagen solution as it is extruded. Prior to use in the engineered implant the collagen fibers are sterilized by peracetic acid sterilization.

C. Engineered Muscle Cells

Any type of muscle cells can be used in the present invention, including cell culture strains, transformed cells, primary muscle cells, embryonic muscle cells, neonatal muscle cells, embryonic stem cells, etc. Preferred cells are stem cells or muscle cells (or muscle precursor cells) which are obtained from a host into which the muscle will be transplanted. Barrofio, A., et al., Identification of Self-Renewing Myoblasts in the Progeny of Single Human Muscle Satellite Cells, 1996 Differentiation 66:47–57; Blau, H. M. and Webster, C., Isolation and Characterization of Human Muscle Cells, 1981 Proc. Natl. Acad. Sci 78:5623–27. The term "primary myocytes" means muscle cells which are obtained directly from a host animal muscle which retain the ability to differentiate and which have been passed a minimum number of times in culture. Such cells generally are not transformed.

The cell type to be used in the implant depends upon use and the site of implantation that is to be reconstructed repaired or otherwise augmented by the engineered muscle. A variety of cell types can be used and include but are not limited to; embryonic stem cells, bone marrow stem cells, satellite muscle cells from the striated muscle beds, cardiac muscle cells, smooth muscle cells, muscle cell lines, transformed cell lines and genetically engineered cell lines. Cells isolated from fetal, neonatal and adult tissue may be used. Fetal cardiac myocytes can be used in the construction of the cardiac prosthesis. Cells of the c2c12 muscle cell line can be used for the fabrication of skeletal muscle implants. In the long run a stem cell population (adult or embryonic) will be the ideal cell source for the fabrication of the muscle. Stem cells are attractive for this use because they can be engineered to become nearly any type of cell (e.g., smooth muscle, cardiac muscle, skeletal muscle, cartilage, bone, etc). They can but do not have to come from the patient to be treated with the muscle implant, because even if they come from some other source they will not invoke an immune response.

For skeletal muscle, satellite muscle cells are derived from a suitable, and unobtrusive, donor site on the subject who is to receive the muscle implant. Muscle biopsies are isolated, and the connective tissue removed by dissection. Various protocols can be utilized to isolate satellite or other cell types from the muscle for engineering the implant. For instance, a protocol can be as follows: Isolated muscle tissue is minced and dissociated into a single cell suspension, by trypsin-EDTA digestion (or other suitable enzymes) under constant stirring. At the conclusion of the enzymatic dissociation procedure, the digestion media is quenched with the addition of 10% serum. Cell suspensions are washed by centrifugation, and a sample is stored in liquid nitrogen for future use. The balance of the isolated cells are enriched in satellite cells by flow cytometry or through the use of differential adhesion or through immunoseparation methods. Flow cytometery, can be used to separate cells by size, by cell cycle stage, or, if labeled, by cell surface markers. In differential adhesion, cells are placed into a culture vessel for a short incubation period to allow contaminating fibroblasts to seed out of the solution, thus enriching the remaining cell population in satellite cells. A longer interval of differential adhesion can be used to seed out satellite cells so they can be purified away from contaminating debris and muscle cells. Enriched cell fractions that contain myogenic satellite cells can be stored at −70° C. in liquid nitrogen. Regardless of the technique used to isolate and purify satellite cells the samples are thawed and plated into culture vessels and assayed for myogenic potential. Cell lots that are competent to undergo differentiation are used in the fabrication of the muscle implant. After partial purification, clones are assayed for myogenic potential, e.g., by plating cells onto collagen—coated dishes and observing whether adherent cells display the characteristics of muscle cells.

Candidate clones from the primary cell isolate are grown under sparse culture condition (i.e. low cell density) in an appropriate media, e.g., containing 10–15% serum, to accumulate an adequate number of cells from which the implant can be fashioned. Once a sufficient number of cells have been obtained (dependent upon the size of the implant to be fabricated), they are prepared for insertion into the bioreactor for the assembly of the prosthetic muscle. Muscle cell differentiation in the bioreactor can be induced by replacing the high serum content media (10–15% serum) with low serum media.

Cells utilized in the fabricated muscle are readily amenable to genetic manipulation. For example, genes encoding angiogentic factors, growth factors or structural proteins can be incorporated into the isolated cells. This can be accomplished before, during or after the fabrication of the muscle construct. Useful genes include, e.g., VEGF, FGF, and related genes. For introducing genes into cells, any effective method can be used, including viral vectors, such as adenovirus, also DNA, plasmids, etc. can be used.

D. Assembly of an Engineered Skeletal Muscle Implant

The muscle implant can comprise three distinct components, the extracellular matrix, the engineered tendon and the population of muscle cells. As detailed earlier, an extracellular matrix composed of a matrix of collagen fibers or other biologically compatible material is prepared on the outer surface of the inner cylinder of an RCCS bioreactor (or suitable substitute). The structural properties of this mat of fibers are regulated by the diameter of fibers produced, the relative concentration of materials used in the reaction (e.g. concentration of type I to type III collagen, or other incorporated materials), and other reaction conditions.

Figure 3:
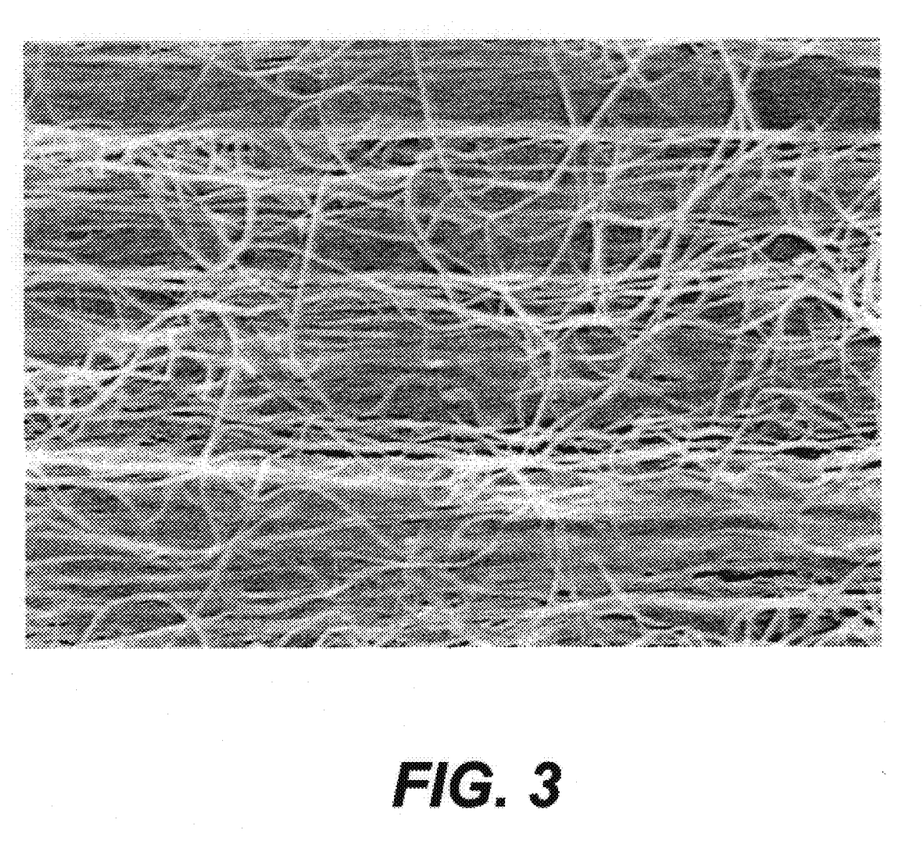
FIG. 3 is a scanning electron micrograph of a thin gel of aligned collagen.

In one preferred embodiment, a thin gel matrix of collagen or other suitable matrix material can be applied over the surface of the extracellular matrix to enhance muscle cell adhesion, differentiation, and/or alignment. The gel matrix can be applied in any suitable manner including electrospinning, spraying, dipping, spreading, dropping, etc. Simpson, et al., Modulation of Cardiac Phenotype in vitro by the Composition and Organization of the Extracellular matrix, 1994 J. Cell Physiol. 161:89–105. In a preferred embodiment, the collagen fibers in the thin gel are aligned along a common axis. For example, the aligned matrix can be produced by dipping the central cylinder core of the RCCS bioreactor, with its electrospun coating of collagen, end-on into a ice cold neutral stock solution of collagen (1 mg/ml) (Type I or type III or a mixture thereof). After a very brief interval (1–3 secs), the cylinder is removed from the solution and the excess collagen is allowed to drain by gravity off of the distal end of the cylinder. The orientation of the cylinder is maintained constant throughout this process, i.e. perpendicular to the collagen solution in which it was dipped. This allows the excess collagen to drain off the long axis of the cylinder. The cylinder is then placed into an incubator, e.g., set for 37° C, to allow the collagen to polymerize, e.g., sixty minutes or more. After polymerization is complete, the aligned collagen fibers are allowed to dry down on to the underlying facial sheath. These procedures result in a thin layer of aligned collagen fibrils arrayed along the axis the cylinder was drained. See FIG. 3. Other methods for aligning the collagen may be employed, for instance, using the described electrospinning system or using a centrifuge after dipping the core in the collagen solution. Regardless of how the collagen is aligned, at the conclusion of this step, the central RCCS cylinder has a mat-like coating of electrospun collagen fibers (the extracellular matrix) covered or coated with a thin layer of aligned collagen.

If desired, the extracellular matrix can incorporate other materials as well, such as polyester mesh and other synthetic materials.

Also, as discussed earlier, the need for the thin gel of collagen fibers may be obviated if the electrospun matrix is sufficiently oriented during the electrospinning process. In other words, the additional thin gel layer of oriented collagen is only necessary if the extracellular matrix (fascial sheath in the example of skeletal muscle) of collagen or other polymer is unoriented.

Large diameter, extruded collagen fibers (engineered tendons) are then applied over the aligned collagen gel. The mechanical properties of the implant are controlled in this step at two separate sites. First, by the thickness of the individual extruded fibers and the number of these filaments added to the implant. Second, by the orientation of these fibers with respect to the long axis of prosthesis. The implant can be made more or less stiff by applying these fibers in an undulating pattern. The large fibers can also be attached to the matrix by only overlapping the matrix at the distal ends, i.e., not necessarily running the entire length of the engineered muscle. Regardless of the orientation used, the ends of extruded fibers are allowed to project from the distal ends of the implant. At the conclusion of this step, the large diameter collagen fibers are allowed to dry down onto the fibers of the aligned collagen gel. Alternative fabrication processes can be used to further customize the mechanical properties of the implant. For example, large diameter collagen fibers may be laid down first followed by collagen fibers deposited by electrospinning, followed by another layer of large diameter collagen fibers, the aligned collagen gel and the satellite cells. Other permutations on this assembly process are also possible.

A tendon can also be created in situ by combining tendon fibroblasts with the synthetic muscle bed. For example, tendon fibroblasts may also be harvested from a recipient's own tendon. These cells are placed on the end of the muscle bed synthesized as described herein. The tendon is allowed to grow with the muscle bed in the bioreactor. The tendon fibroblasts are encouraged to grow in an oriented fashion by use of the aligned substrate herein or by other orientation methods. If this method is chosen, the extruded collagen tendons described herein become unnecessary, although a combination of extruded and cultured tendons may be desired for certain applications.

In the final step of the fabrication process, the inner cylinder with its engineered fascial sheath and overlaying layers of aligned collagen and large diameter collagen fibers is loaded into a RCCS bioreactor. Muscle cells, such as satellite myoblasts isolated from the subject or compatible donor, are loaded into the chamber and allowed to interact with the collagen-based substrate. The RCCS bioreactor is preferably used in this step because it provides high nutrient profusion in a very low shear environment. However, other culture vessels can be used. Under these conditions, it is possible to assemble a muscle cell culture comprising multiple layers (8–12 layers in 48 hours) of aligned cells. In the assembly of the muscle implant, cells are gradually depleted from suspension culture and plated onto the collagen matrix, either directly on the electrospun matrix or on the collagen gel coating, to form the three dimensional arrangement of the engineered tissue. Additional satellite cells are added as need to the bioreactor to assemble additional cell layers. Once the desired mass of cells has been plated onto the fascial sheath, they are allowed to differentiate into myotubes, e.g., by transfer to a serum media. Also, there are artificial oxygen carriers that can be used in vitro to increase oxygen delivery to tissues or cells in culture. They would be mixed into the reactor with the satellite cells as the muscle is fabricated. They basically function like red blood cells.

Any suitable culture media can be used to grow the cells, including medias comprising serum and other undefined constituents, defined medias, or combinations thereof, RPMI, etc.

Figure 5A:
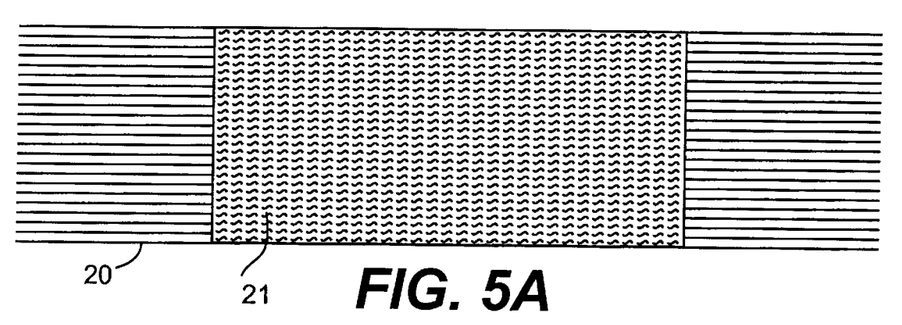
FIGS. 5A and 5B are schematic representations of how a muscle implant may be fabricated.
Figure 5B:
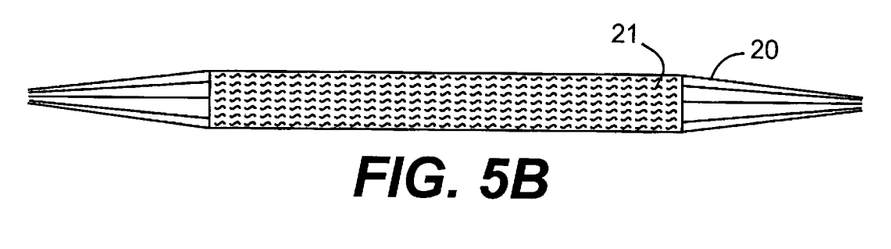

With the completion of the differentiation process, the skeletal muscle implant is ready for transplantation into the site of reconstruction in the subject. The implant is removed from the central cylinder of the bioreactor. The size and thickness of the implant is controlled at this stage of the process at two different levels—first, by the number of cell layers assembled onto the central cylinder and, second, by the size of the sheet of tissue used to construct the muscle implant. This latter procedure involves trimming (for instance, into a rectangular sheet—FIG. 5A), stacking, and rolling (FIG. 5B) the engineered muscle into the desired configuration. Alternatively, the engineered muscle can be directly implanted or layered for the reconstruction of, for instance, facial muscles as a flat sheet. If the engineered muscle is to be used to reconstruct a muscle bed of the axial skeleton, it may be attached to the implantation site through the large diameter collagen fibers 20 that protrude from the ends of engineered muscle 21, through the distal ends of the fascial sheath itself or through a combination of these methods.

If the tissue is to be used to reconstruct a congenital heart defect or repair an otherwise dysfunctional region of myocardium or reconstruct a muscle of facial expression it can be sutured or affixed in place with fibrin glue. By modifying the assembly process, implants for the reconstruction of cardiac muscle or smooth muscle can be assembled. In general, the major modification may be in the relative pattern of the engineered extracellular matrix and connective struts or tendons described in this application. Cardiac tissue and smooth muscle lack tendons. However, the use of large diameter collagen fiber may still be desirable to lend mechanical strength to the implant. In the case of cardiac implants, the large fibers may be used as a delivery system to assemble the implants. The key common feature to assembly of these implants is the ability to fabricate a multi-layer implant composed of cells in an in vivo pattern of organization.

Vascularization of the implanted muscle tissue will occur in situ several days after surgery. It can be stimulated further, as mentioned above, by angiogenetic and growth-promoting factors, either administered as peptides or as gene therapy.

The engineered muscle described above is advantageous in several respects. First, the connective backbone support of the implant comprises natural materials. This material has low antigenic potential and its structural properties can be regulated at many different sites, including, but not limited to; the relative concentration of different collagen isoforms used to produce the sheath, the thickness of the fibers used and, the degree of chemical cross-linking present in the matrix. Next, the implant uses large diameter collagen fibers to further modify the structural properties of the implant and provide a means to anchor the engineered muscle to the site of transplantation. These fibers are very similar to the fibers used to manufacture catgut for surgical sutures (>250 µm), however, the extrusion process allows for better control of fiber diameter and the fabrication of fibers that are much smaller in diameter than conventional catgut (50 to 200 µm depending upon reaction condition). Preliminary studies from other laboratories indicate the efficacy of using extruded collagen fibers in the production of tendons in the rat and in the formation of woven sheets for the repairs of experimental abdominal wounds in the rat. The implantation of large diameter, extruded collagen fibers did not induce inflammation beyond background levels in these experiments.

The stem cells or muscle cells used to construct the implant can be isolated from the subject, or other compatible donor, that requires muscle reconstruction. This has the obvious advantage of using cells that will not induce an immune response, because they originated with the subject (autologous tissue) requiring the reconstruction. Relatively small muscle biopsies can be used to obtain a sufficient number of cells to construct the implant. This minimizes functional deficits and damage to endogenous muscle tissues that serves as the donor site for satellite muscle cells.

Another factor unique to this muscle prosthesis is the shape of the individual muscle cells and their three-dimensional arrangement. The cultures are composed of linear, three-dimensional arrays of muscle cells distributed along a common axis in an in vivo-like pattern of organization. This makes it possible to install an implant that can produce contractile force along a defined direction, allowing for the structural and functional repair of a dysfunctional muscle bed. Cultures prepared on, or, in a random gel of collagen lack this uniform alignment. Compare FIG. 4A (aligned) with FIG. 4B (random). Random cultures are unsuitable for the use in reconstruction because they lack the clearly defined orientation that is characteristic of intact skeletal muscle and the individual cellular layers of the heart. The highly polarized nature of intact muscle allows it to effectively and efficiently apply mechanical force along a defined axis during contraction. This property also facilitates the conduction of electrical impulses through the tissue.

Strategies must be implemented to promote the formation of vascular elements within the implant. Several options are available. First, the implants can be seeded with angioblasts and/or endothelial cells to accelerate the formation of vascular elements once the engineered tissue is placed in situ. Second, angiogenic peptides can be introduced into the engineered tissue via an osmotic pump. The use of an osmotic pump makes it possible to deliver active peptides directly to the site of interest in a biologically efficient and cost-effective manner. Experimentation in the vascular bed of ischemic skeletal muscles has demonstrated the efficacy of this approach (Hopkins et al., Controlled delivery of vascular endothelial growth factor promotes neovascularization and maintains the limb function in a rabbit model of ishemia, 1997 J. of Vascular Surgery 27:886–95). VEGF delivered to ischemic hind limbs of rabbits accelerated capillary bed growth, increased vascular branching and improved muscular performance with respect to ischemic controls. Upon initial implantation, an early phase of muscle degeneration of intact muscle implants (Faulkner et al., Revascularization of skeletal muscle transplanted into the hamster cheek pouch: Interavital and light microscopy, 1983 Microvasular Res. 26:49–64) suggests that it may be desirable to implant engineered muscle tissue at a time just prior to muscle differentiation. An alternative approach is to "seed" fully differentiated muscle constructs with additional satellite cells and/or endothelial cells and or angioblasts shortly before they are implanted in situ.

Figure 6:
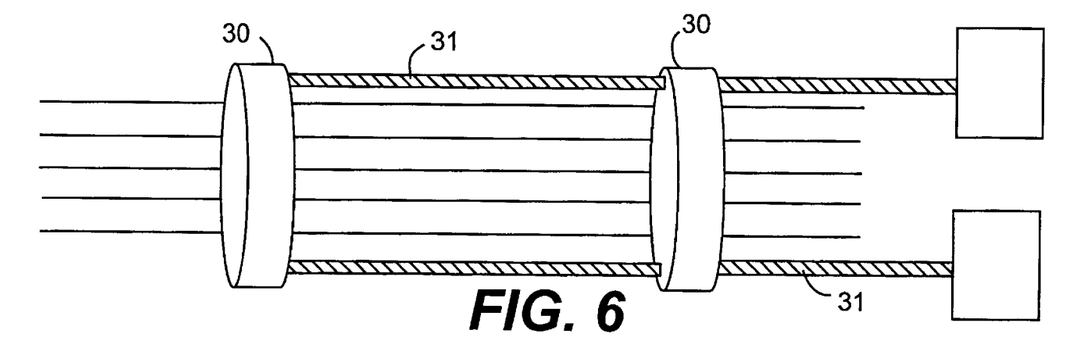
FIG. 6 is a schematic representation of one type of hypertrophy mechanism.

In vivo deneravation of skeletal muscle promotes the evolution of atrophy in the effected tissue. To a great extent, this response appears to develop because deneravation reduces the amount of resting tension observed in the affected muscle (Thomsen and Luco 1944; Gutman et al., 1971). In vitro, the effects of denervation may be substantially overcome by applying tension to the denervated muscle. Cardiac muscle is also very sensitive to its surrounding medical environment. Muscle mass may be initially retained in an engineered prosthesis by placing it under tension at the time it is implanted. Different methods of hypertrophy or stretching of the implant are available. A mechanical stretcher can be used in the bioreactor by attachment of the "tendons" on either end of the implant to ring clamps to tighten or loosen the implant. FIG. 6 illustrates how the fibers will be held in place (at desired orientations longitudinally) on the inner cylinder surface of the bioreactor by two end supports 30. FIG. 6 also illustrates the use of motor driven screw 31 drives to be added to the bioreactor to allow mechanical stretching (well defined percentage of stretch) for preconditioning particular tissue (muscle, blood vessels, and intestines) during the initial cell seeding/development stage. The stretching makes bigger, thicker and stronger cells/tissue that are less likely to tear after implantation. The stretching can also be used to further align the muscle cells. Electrical pacing or pharmacological stimulation can also be used. Electrical pacing, in particular, is very effective and easy to control.

The second level of control that is imparted by the central nervous system on skeletal muscle is more fundamental. Neural inputs directly control the action of the tissue. In order to achieve a fully functional muscle prosthesis it is necessary to bring it under the control of the central nervous system. Preferably, the engineered implant can be transplanted into a muscle bed adjacent to the area of interest and allowed to adapt to the in vivo environment. After a period of adaptation the autologous implant would be mobilized, perhaps with a portion of the motor units arising from the original transplant site, and repositioned within the site requiring reconstruction. It may also be possible to induce the ingrowth of motor neurons through the use of growth peptides delivered by osmotic pumps, or other means, to the implant tissue. Cardiac tissue mass is not subject to much regulation by the central nervous system. However, it is sensitive to changes in mechanical activity. By pre-stressing by stretching, electrical stimulation or using pharmacological agents to promote cardiac muscle hypertrophy an implant of cardiac muscle during or following the fabrication process, it can be better prepared for the region of the in vivo environment.

Example 1 Electrospinning an Extracellular Matrix

An extracellular matrix was made of poly-lactic/polyglycolyic acid (PLA/PGA; 50/50—RESOMER® RG 503, Boehringer Ingelheim, Germany) and poly(ethylene-co-vinyl) acetate (Aldrich Chemical Company, Inc., Milwaukee, Wis.) polymers. The concentration of the two polymers dissolved in dichloromethane (Sigma-Aldrich, St. Louis, Mo.) were 0.19 g/ml RESOMER® RG 503 and 0.077 g/ml poly(ethylene-co-vinyl) acetate. The electrospinning set-up consists of a glass pipet (overall length approximately 21 cm with a tapered tip with an opening estimated at 0.3 mm, no exact measurement obtained, 0.32 mm diameter silver-coated copper wire, 20×20 mesh 316 stainless steel screen, two large clamp holders (polymeric coated), base support, and a Spellman CZE1000R power supply (0–30,000 volts, Spellman High Voltage Electronic Corp., Hauppauge, N.Y.). The physical set-up had the top clamp holder containing the glass pipet at approximately 12 inches from the base with the pipet tip pointing (pipet at approximately at 45 angle to base) toward the base. The wire was then placed in the top of the glass pipet and inserted until reaching the pipet tip where it remained during the procedure. The second clamp holder was placed at approximately 6 inches above the base for holding the screen (grounded target) approximately perpendicular to the axis of the glass pipet. The distance between the pipet tip and the grounded screen was approximately 10 cm. The positive lead from the high voltage power supply was attached to the wire hanging out the top end of the glass pipet while the negative lead (ground) was attached directly to the stainless steel screen. The glass pipet was then filled with the appropriate solution and the power supply turn on and adjusted until electrospinning was initiated (i.e. fibers shooting from the tip of the glass pipet). This stream (splay) of solution begins as a monofilament which between the pipet tip and the grounded target is converted to multifilaments (electric field driven phenomena). This allows for the production of a "web-like" structure to accumulate at the target site. Upon reaching the grounded target, the multifilaments collect and dry to form the 3-D interconnected polymeric matrix (fabric). The apparatus described is conceptually the same as the set-up illustrated in FIGS. 2A and 2B. All described studies and solutions are at room temperature. The fibers produced by these preliminary studies ranged from 1–100 microns in diameter with both polymeric solutions evaluated. The thickness of the matrices produced was not measured. Although, the thickness of the matrix that can be produced is dependent on the amount of polymer solution (spinning time) utilized and allowed to accumulate in a particular region. Thus, allowing the ability to produce a matrix with varying thickness across the sample. A scanning electron micrograph of the fiber forming the matrix is shown in FIG. 1.

Example 2 Fabrication of a Three Dimensional Segment of Skeletal Muscle

An aligned collagen gel was prepared after the methods of Simpson et al., 1994 (Journal of Cell Physiology) on a silastic membrane (Specility Manufacturing). Silastic membranes were sterilizied in an autoclave and exposed to 2 minutes of electrical discharge to make the rubber more hydrophlic. Aligned collagen was then applied over the surface of the treated silastic rubber. In brief, 500 µl of 0.2 N HEPES was mixed with 500 µl of 10×MEM in a 50 ml centrifuge tube and placed on ice. Under sterile conditions 3.5 mls of Type I collagen (3 mg/ml in 0.012 HCL, Collagen Corporation) was layered over the top of the HEPES/10× MEM solution, mixed by inversion and diluted to a final volume of 10 mls with ice cold Phosphate Buffered Saline. A sterile and treated silastic membrane (70 mm×30 mm) was placed in a 100 mm culture dish. One milliliter of ice cold collagen solution (final concenration 1.05 mg collagen/ml solution) was applied to the one end of the rectangular piece of silastic membrane. The collagen was pulled in a single continuous stroke across the long axis of the silastic membrane with a sterile cell scraper. The dish containing the silastic membrane was then tipped and the collagen was allowed to drain across the membrane along the axis that it was applied. The dish was covered and placed into a 37 degree Celsius incubator for 1 hour to allow the collagen to undergo polymerization. These procedures resulted in a thin layer of aligned collgen fibrils on the silastic membrane. The membranes were then allowed to dry in a moist atmosphere for 12–24 hours. This allows the collagen to partially dry down without pooling the collagen and disturbing the aligned collagen fibrils. The silastic membranes were then allowed to completely dry for an additional 30–60 minutes under a sterile laminar flow hood. Complete drying of the collagen anchors the fibrils to the rubber for further manipulation. Silastic membranes were used in these experiments solely to provide a support surface that could be easily manipulated for the fabrication of the engineered muscle.

A segment of silastic membrane (22 mm×22 mm) containing uniformly arrayed collagen fibrils was cut and transferred to a sterile 35 mm culture dish. Cells of the mouse c2c12 skeletal muscle cell line were placed onto the silastic membranes and cultured for 3–5 days in DMEM-F12 (50:50 DMEM:F12 mix, supplemented with 10% Horse serum, 5% FBS plus penstrep and gentimysin) and allowed to form a confluent culture of uniformly arrayed cells. These cultures served as a template layer for the further assembly of the cultures. A thin layer of silicon grease was placed on the underside of a piece of silastic rubber containing a culture of aligned c2c12 cells. The silicon grease serves as a non-toxic adhesive to anchor the culture to different locations within the culture chamber of a RCCS Bioreactor (Synthecon, Inc). In preliminary experiments several different locations in the bioreactor culture vessel were used in attempts to fabricate a three dimensional array of aligned muscle.

An aligned culture of c2c12 cells was placed on the back wall of the rotating bioreactor culture vessel, cell side up and held in place by a thin layer of silicon grease. The vessel was closed and then filled with culture media (50:50 DMEM:F12 mix, supplemented with 10% Horse serum, 5% FBS plus penstrep and gentimysin). The syringe ports were opened and 1 million c2c12 cells were added as a single cells suspension to the bioreactor vessel. The device was mounted on the control axle that controls the rotational rate of the vessel. The entire device was then placed into a C02 incubator (37° C.) and set to rotate at 3 revolutions per minute. At 24 hour intervals an additional 1 million c2c12 cells were added to the reactor chamber.

By setting the rate of rotation at a slow rate the cells added in suspension were gradually seeded out onto the template culture. After 48 hours of mixing in the vessel, the template cultures were isolated and prepared for electron microscopic examination. The cultures prepared in the RCCS reactor were composed of multiple layers of c2c12 cells arrayed along a common axis. Several different locations and conditions within the bioreactor were assayed for the ability to fabricate the multi-layered cultures. In this experimental run, it was found that cells arrayed on the back wall of the reactor in an orientation that was perpendicular to the direction of rotation was most effective. Other sites within the vessel also promoted the assembly of multilayered cultures, including the outer wall, central core and outer cylindrical wall. Aligned cultures that were oriented with the direction flow were also capable of promoting multlayer assembly, although not as effectively as the cultures oriented perpendicular to the direction of rotation.

In other experiments, an aligned collagen gel was prepared on a silastic membrane as described and placed directly into the RCCS bioreactor chamber (i.e. the experiments were designed to determine if the aligned collagen fibrils could promote multilayered assembly without first growing a confluent template layer of cells). Templates consisting of aligned collagen alone were about as equally effective as the templates containing confluent cell layers at promoting the assembly of the multilayered cultures. Again, these collagen templates were placed onto the bioreactor in different locations. They behaved identically as the confluent cell layers, i.e. collagen coated membranes of the back wall oriented perpendicular to the axis of rotation were most effective at promoting multilayer assembly.

Figure 4A:
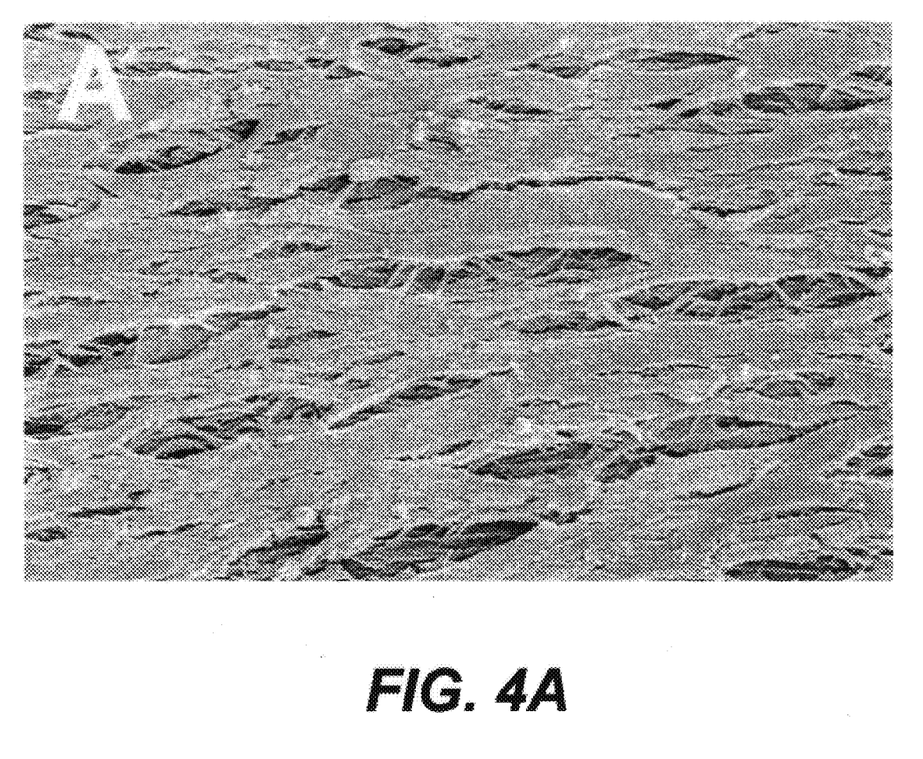
FIGS. 4A and 4B are scanning electron micrographs of muscle cells deposited on aligned collagen gel and a random collagen gel respectively.
Figure 4B:
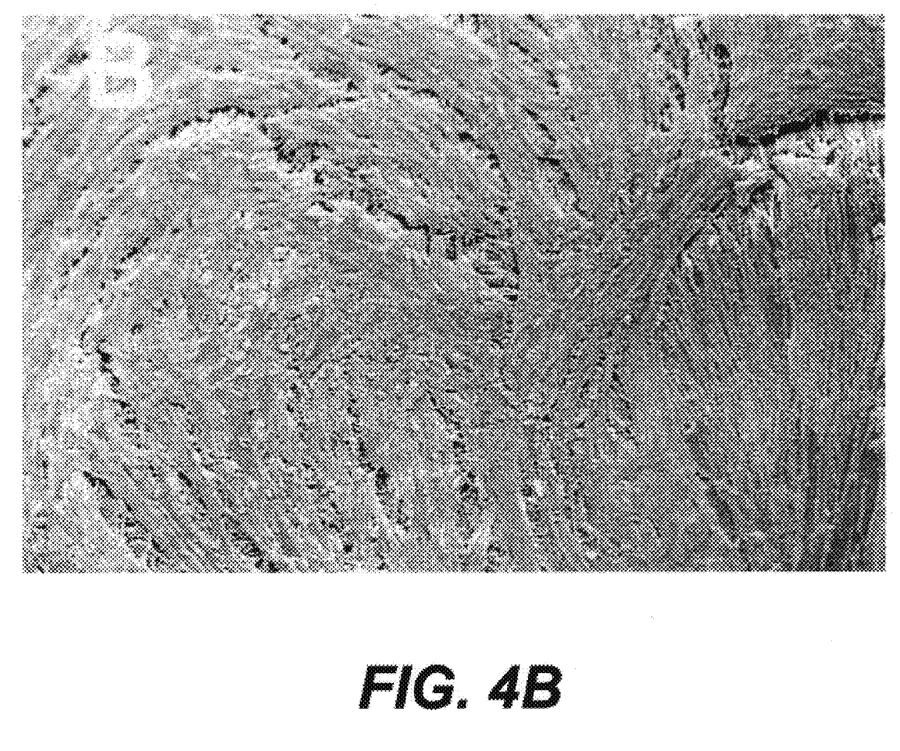

A scanning electron micrograph of the muscle cells deposited on the aligned collagen is shown in FIG. 4A.

Without further elaboration, it is believed that one skilled in the art can, using the proceeding description, utilize the present invention to its fullest extent. The preceding preferred specific embodiments are, therefore, to be construed as merely illustrative, and not limiting the remainder of the disclosure in any way whatsoever. The entire disclosure of all applications, patents, and publications, cited above and in the figures are hereby incorporated by reference in their entirety.

What is claimed is:

1. A muscle implant comprising:
   an extracellular matrix for supporting muscle,
   a tendon comprising extruded fibers,
   a muscle cell layer, and
   an oriented layer of collagen deposited onto the extracellular matrix wherein the muscle cells are disposed onto the oriented layer of collagen.
2. The muscle implant as described in claim 1, wherein the muscle cell layer is multilayered.
3. The muscle implant as described in claim 1, wherein the muscle cells and tendon are oriented in parallel directions.
4. A muscle implant comprising an extracellular matrix for supporting muscle, a muscle cell layer, and an oriented layer of collagen deposited onto the extracellular matrix wherein the muscle cells are disposed onto the oriented layer of collagen.
5. The muscle implant as described in claim 4, wherein the muscle cell layer is multilayered.
6. A method of forming a muscle implant comprising:
   providing a fascial sheath,
   depositing a layer of collagen on the fascial sheath,
   laminating a tendon onto the fascial sheath, and
   depositing muscle cells onto the collagen.
7. The method described in claim 6, further comprising: aligning the layer of collagen on the fascial sheath.
8. The method described in claim 6, further comprising: laminating the tendon onto the fascial sheath in the same direction as the alignment of the collagen.
9. The method described in claim 6, wherein the tendon is formed by extruding collagen fibers.
10. The method described in claim 6, wherein the muscle cells are satellite muscle cells obtained from a patient into which the muscle implant will be placed.
11. A method of layering muscle cells on an extracellular matrix comprising:
    providing an extracellular matrix,
    placing the extracellular matrix inside a rotating wall bioreactor,
    loading a culture medium into the bioreactor wherein the medium comprises muscle cells, and
    running the bioreactor until muscle cells attach to the extracellular matrix.
12. The method described in claim 11 wherein the muscle cells attached to the extracellular matrix form multiple layers.

* * * * *